(12) United States Patent
Dana et al.

(10) Patent No.: US 12,268,449 B2
(45) Date of Patent: Apr. 8, 2025

(54) INTRAOCULAR PRESSURE MONITORING DEVICES AND METHODS OF USING THE SAME

(71) Applicant: Smartlens, Inc., Mountain View, CA (US)

(72) Inventors: Aykutlu Dana, Mountain View, CA (US); Sevda Agaoglu, Mountain View, CA (US); Murat Baday, Mountain View, CA (US); Savas Komban, Mountain View, CA (US); Ahmet Taylan Yazici, Mountain View, CA (US)

(*) Notice: Subject to any disclaimer, the term of this patent is extended or adjusted under 35 U.S.C. 154(b) by 773 days.

(21) Appl. No.: 17/495,198

(22) Filed: Oct. 6, 2021

(65) Prior Publication Data

US 2022/0022744 A1    Jan. 27, 2022

Related U.S. Application Data

(63) Continuation of application No. PCT/US2020/002721, filed on Apr. 8, 2020.

(60) Provisional application No. 62/832,151, filed on Apr. 10, 2019.

(51) Int. Cl.
*A61B 3/16*    (2006.01)
*A61B 5/00*    (2006.01)

(52) U.S. Cl.
CPC .............. *A61B 3/16* (2013.01); *A61B 5/6821* (2013.01); *A61B 2562/0261* (2013.01)

(58) Field of Classification Search
None
See application file for complete search history.

(56) References Cited

U.S. PATENT DOCUMENTS

| | | | |
|---|---|---|---|
| 3,406,681 A | 10/1968 | Felix | |
| 4,981,342 A * | 1/1991 | Fiala | G02B 3/10 351/159.05 |
| 6,110,110 A | 8/2000 | Dublin, Jr. et al. | |
| 6,250,757 B1 * | 6/2001 | Roffman | G02C 7/042 351/159.7 |
| 10,016,132 B2 | 7/2018 | Mandel et al. | |
| 10,085,637 B2 | 10/2018 | Araci et al. | |
| 10,219,696 B2 | 3/2019 | Araci et al. | |
| 11,213,203 B2 | 1/2022 | Mandel et al. | |
| 11,759,107 B2 | 9/2023 | Araci et al. | |

(Continued)

FOREIGN PATENT DOCUMENTS

| | | |
|---|---|---|
| JP | 2012239530 A | 12/2012 |
| JP | 2013544558 A | 12/2013 |

(Continued)

OTHER PUBLICATIONS

Anonymous. "Photoelasticity", Wikipedia. Apr. 5, 2019. Retrieved from the Internet: https://en.wikipedia.org/w/index.php?title=Photoelasticity&oldid=891014204.

(Continued)

*Primary Examiner* — May A Abouelela
*Assistant Examiner* — Samuel C Kim
(74) *Attorney, Agent, or Firm* — WILSON SONSINI GOODRICH & ROSATI

(57) ABSTRACT

Described herein are various devices, systems and methods for measuring the intraocular pressure of an eye using a stress or pressure sensor placed on or in the eye.

20 Claims, 18 Drawing Sheets

(56) References Cited

U.S. PATENT DOCUMENTS

| | | |
|---|---|---|
| 2011/0313272 A1 | 12/2011 | Steinmueller |
| 2012/0143325 A1* | 6/2012 | Christie ................ G02C 7/046 623/5.13 |
| 2016/0067035 A1* | 3/2016 | Gontijo ................ A61F 2/1601 408/1 R |
| 2017/0251921 A1* | 9/2017 | Phan ........................ A61B 3/16 |
| 2017/0280997 A1* | 10/2017 | Lai ........................ A61B 5/0077 |
| 2019/0076021 A1 | 3/2019 | Araci et al. |
| 2021/0298677 A1 | 9/2021 | Dana et al. |
| 2023/0380686 A1 | 11/2023 | Araci et al. |

FOREIGN PATENT DOCUMENTS

| | | |
|---|---|---|
| WO | WO-2012052765 A2 | 4/2012 |
| WO | WO-2014137840 A1 | 9/2014 |
| WO | WO-2015159836 A1 | 10/2015 |
| WO | WO-2020060558 A1 | 3/2020 |
| WO | WO-2020124074 A1 | 6/2020 |

OTHER PUBLICATIONS

EP20786874.6 Extended European Search Report dated Dec. 5, 2022.

\* cited by examiner

INTRAOCULAR PRESSURE MONITORING DEVICES AND METHODS OF USING THE SAME

CROSS-REFERENCE TO RELATED APPLICATIONS

This application is a continuation of PCT Application No. PCT/US2020/027221, filed Apr. 8, 2020, which claims priority from U.S. Provisional Application 62/832,151 entitled "Intraocular Pressure Monitoring Method and Devices Using the Same," filed Apr. 10, 2019, the contents of which are hereby incorporated by reference in their entirety.

BACKGROUND

The present disclosure relates to a method, system and devices for Intraocular Pressure (IOP) sensing.

Photoelasticity describes changes in the optical properties of a material under mechanical deformation. It is a property of all dielectric media and is often used to experimentally determine the stress distribution in a material, where it gives a picture of stress distributions around discontinuities in materials.

BRIEF SUMMARY

Described herein are systems, devices and methods for intraocular pressure sensing using photoelastic material in combination with other materials. The process involves the placement of a sensor on or in an eye using either a contact lens or intraocular lens respectively. The lens contains a sensor made from a photoelastic material. As the pressure in the eye changes, the radius of curvature of the eye may change, and produce a stress effect on a contact lens sensor. Alternatively, for an implanted intraocular lens, the pressure change can be measured directly by measuring the pressure on the intraocular lens. The pressure and stress changes cause the photoelastic material to change shape, and alter the transmission of reflected light. This altered reflectance can be captured, analyzed and correlated to a known change in IOP to produce an accurate measurement of the IOP of an eye.

In some embodiments, there may be a device for conforming to the surface contour of an eye. The device comprises a body composed of a biocompatible material and shaped to resemble a contact lens, a stress sensor embedded within the body. The stress sensor may have an annular ring having a central aperture, and a plurality of secondary apertures arranged around the central aperture, the plurality of secondary apertures defining a plurality of struts, the annular ring may be made of a photoelastic material. The shape of the annular ring, the aperture and the plurality of secondary apertures defines a foot print of the annular ring. A reflector material may be layered under the annular ring, the reflector material having substantially the same foot print as the annular ring. The struts of the annular ring will flex in response to changes in the surface contour of the eye.

In some embodiments, there may be a photoelastic intraocular lens (PEIOL) for measuring an intraocular pressure (IOP) in an eye, the intraocular lens has a body composed of a biocompatible elastomeric material, the body may be configured to fit inside the eye. The PEIOL may have a first support leg, the support leg extending radially from the body. The PEIOL has a photoelastic layer having a center aperture and a plurality of secondary apertures arranged in a ring around the center aperture, the secondary apertures defining a plurality of struts. The struts operate as a plurality of stress concentration features. The photoelastic layer may be embedded in the body. A reflector layer may have a foot print that substantially matches the photoelastic layer. The reflector layer may be adjacent to the photoelastic layer. The PEIOL may also have a first gas filled cavity adjacent to either the photoelastic layer or the reflector layer. Changes in the IOP in the eye exert pressure on the body, and then deformation of the photoelastic layer to produce an optical result.

In some embodiments, there may be a polarimetric measuring device for reading optical data and producing IOP data. The polarimetric measure device has a body and a circuit contained within the body, the circuit has a microcontroller, an analyzer and an interface connector. The polarimetric measuring device also has a light source in electronic communication with the circuit, the light source has a variable controlled through the circuit. There may also be a polarizer with a retarding plate, the retardation plate can condition the output of the light source to produce a particular polarization. A camera may capture images in succession from a PECL or a PEIOL device. The polarimetric measuring device may evaluate the images captured by the camera to calculate an IOP reading for an eye.

In some embodiments, there is a system for measuring the intraocular pressure of an eye. The system may have a deformable sensor suitable for placement on the eye, the deformable sensor may have a biocompatible body and a photoelastic sensor. The system may also have a light source, the light source able to produce various different wave lengths and pulses of light. There may also be an image sensor, the image sensor able to capture light reflected from the photoelastic sensor in the form of image data. The system may also have a mobile computer device for analyzing the image data, and correlated the image data to a set of intraocular pressure levels.

In some embodiments, there is a process for determining the intraocular pressure of an eye. The process involves collecting, via a camera, a plurality of images of a PECL or a PEIOL device under a first lighting condition and a second lighting condition, registering the plurality of images, via a computer, wherein the registering of the plurality of images eliminates a geometrical drift from the plurality of images, filtering, via a computer, the plurality of images, locating, via a computer, a plurality of stress concentration areas in the plurality of images, and analyzing, via a computer, the stress concentration areas to determine an IOP value.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

All illustrations of the drawings are for the purpose of describing selected versions of the various embodiments of the present disclosure and are not intended to limit the scope of the present invention.

Described herein are systems, devices and methods of use related to measuring IOP (intraocular pressure) in an eye. The technology described herein relates to a measurement method, associated devices and miniature readout systems, to allow quantitative determination of intraocular pressure through the use of wearable or implantable lens.

Figure 1:
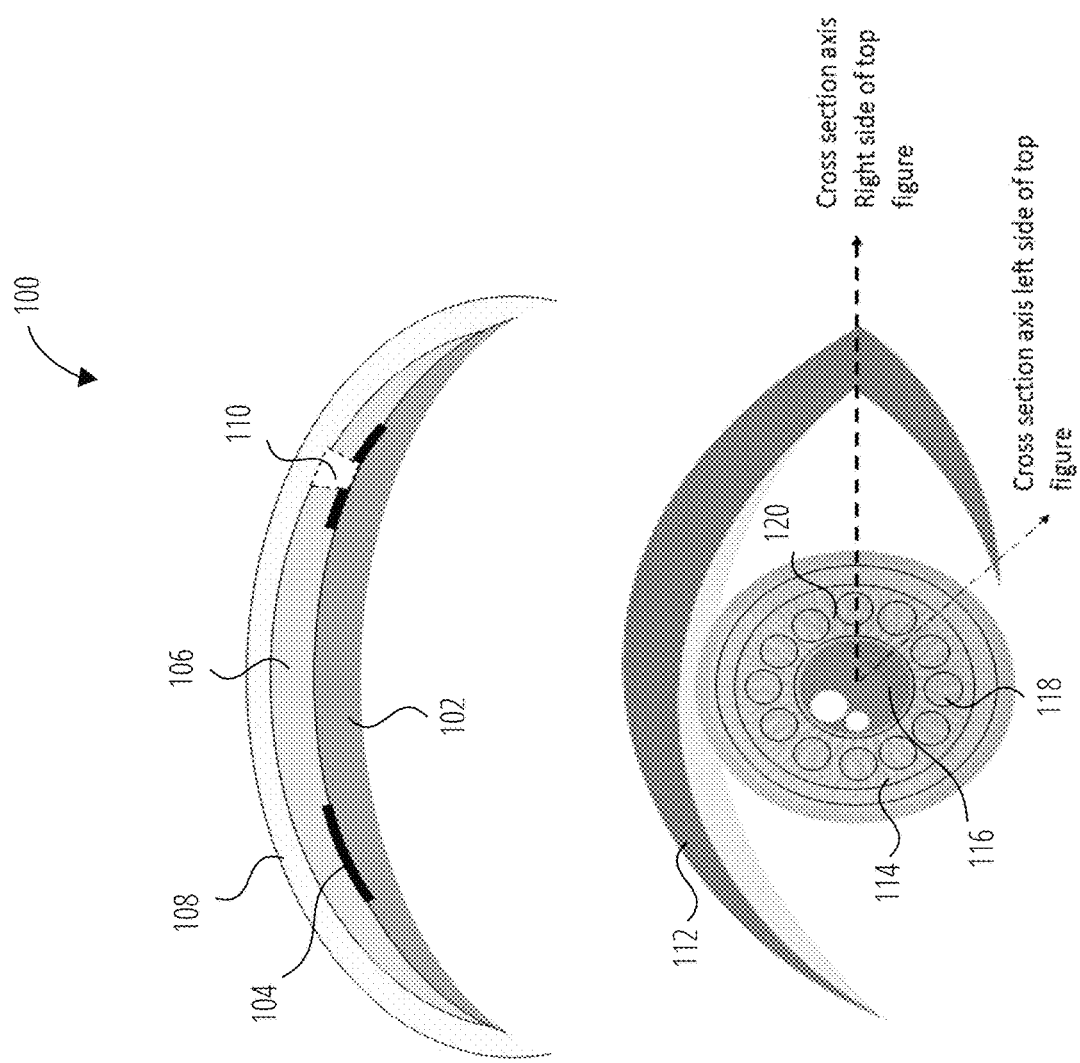
FIG. 1 illustrates an item 100 in accordance with one embodiment.

Referring now to FIG. 1, the cross-section (FIG. 1A) and plan view (FIG. 1B) structure of a photoelastic contact lens (PECL) item 100 are shown. In some embodiments, there is a device for conforming to the surface contour of an eye. The device comprises a body composed of a biocompatible material, and shaped to resemble a contact lens. There may be a stress sensor embedded in the body. The stress sensor may be an annular ring having a central aperture, and a plurality of secondary apertures arranged around the central aperture. The secondary apertures may define a number of struts. The annular ring may be made of a photoelastic material. The shape of the annular ring, the aperture and the secondary apertures may define a foot print of the annular ring. A reflector material may be layered under the annular ring of photoelastic material. The reflective layer may have a foot print that substantially matches the foot print of the annular ring. The struts of the annular ring may flex in response to changes in the surface contours of the eye. The flexing of the annular ring will create deviations in the image reflectance that may be measured and use to quantify the change in the intraocular pressure of the eye.

In an embodiment, the cross section of the PECL shown in FIG. 1A represents the cross section of the rays shown in FIG. 1B. A horizontal ray represented by the heavy dashed line, illustrates the cross section on the right side of FIG. 1A. The right side of FIG. 1A illustrates a cross section through a secondary aperture 118, with a corresponding cut out 110.

The cut out 110 may be filled with a soft material, such as a hydrogel. In another embodiment, the left side of FIG. 1A illustrates the ray of smaller point with alternating dashes and dots. Here the cross section goes through a strut 120 and shows a solid length of the reflector layer 104 with no corresponding cut out 110 above it.

The use of the terms "substantially" or "generally" refers to a degree of flexibility in the nomenclature used herein. Substantially means the component referred to has a leeway of up to +/−20% to the dimension discussed, the dimension may be height, weight, age, thickness or any other quantifiable parameter. In some embodiments, the reflector layer and the photoelastic layer may be substantially the same. That is the foot print of the two may vary by up to +/−20% from each other. In some embodiments, the reflector layer may be up to about 20% larger than the photoelastic layer. In some embodiments, the reflector layer may be up to about 20% smaller than the photoelastic layer. In some embodiments the photoelastic layer and the reflector layer may have matching foot prints. In some embodiments it may not be critical that the photoelastic layer and reflector layer match precisely. There may be deviations in the coverage of one over the other. In general, both may have an open main aperture so as not to interfere with a patient vision. In some embodiments, the device may have similar or same overlapping secondary apertures. In some embodiments, the degree of non-overlapping area of either the reflector layer 104 and the photoelastic layer 106 may be compensated for in the process for determining the stress the sensor 114 may experience. In some embodiments the degree of non-overlap may have no effect on the sensor 114 performance.

The PECL (photoelastic contact lens) may be a multilayer device (item 100) with a base layer 102, a reflector layer 104, a photoelastic layer 106 and a top layer 108. The top layer 108 may be made of a hydrogel, for improved biocompatibility. In some embodiments, the base layer 102 and/or the top layer 108 may itself be a multi layer structure made of two or more different materials. In some embodiments, a multilayer top layer may have a hydrogel layer for user comfort. In some embodiments, any surface that may come into contact with the patient eye or eye lid (such as the base layer or the top layer) may have a hydrogel coating to promote comfort of use. The PECL may be shaped with a radius to match the curvature of an eye, which may be human, animal or artificial. The photoelastic layer 106 may have one or more cut outs or depressions. The cut outs may match the general position of the secondary apertures 118 of the reflector layer 104. Thus when viewed separately, the reflector layer 104 and the photoelastic layer 106 may have similar foot prints that substantially match when laid one on top of the other. By way of an example, one could imagine a cut out paper snow flake as the foot print for the two layers (reflector and photoelastic), and when the two paper snow flakes are laid on top of each other, the shape and orientation of the cut outs may substantially match each other. The reflector layer 104 may be porous, allowing air to pass through the reflector layer 104. In some embodiments, the reflector layer 104 may have nano-pores. In some embodiments, the pores may be smaller or larger. In some embodiments, the size of the pores may act as filters, to prevent the influx of particles in to the sensor.

In some embodiments, the various materials used to make the PECL may be biocompatible materials. An example eye 112 is shown with the pupil and cornea displayed under the PECL. The eye is shown for illustration purposes only and does not represent an element of the technical material described herein. The sensor 114 may be seen placed on top of the eye ball, with the center aperture 116 (the center aperture of the sensor) positioned so as to not obscure the pupil. The reflector layer 104 and the corresponding photoelastic layer may surround the center aperture 116. It may be noted the reflector layer 104 may be opaque or partially opaque to visible light, and have reflective qualities so as to reflect light that may be transmitted through the photoelastic layer 106. Thus light may pass through the photoelastic layer 106, reflect off the reflector layer 104, and pass through the photoelastic layer a second time, prior to being captured by an image sensor. The base layer 102, photoelastic layer 106 and top layer 108 may be substantially transparent to visible light.

In some embodiments, the base layer 102 may be a transparent biocompatible material. In some embodiments the transparent biocompatible material may be an elastomeric material. Examples of such materials include silicone, polydimethylsiloaxane (PDMS) or other transparent and flexible polymers, silicone hydrogels, or hydrogels. In some embodiments, other materials used to make contact lens may also be used, including hard contact lenses of stiffer plastic or glass materials. In some embodiments, the photoelastic layer may be a UV curable epoxy.

In some embodiments, a thin material having reflective properties may serve as a reflector layer 104. The thin material may be a metal or metalized material, or a composite material having the appropriate reflector properties. In some embodiments, the reflector layer 104 may be made of platinum. The reflector layer 104 may be machined or printed to a particular shape as described herein, and having a thickness of about 5 nm or greater.

In some embodiments, the sensor may be between 2 μm and 1000 μm in thickness. In some embodiments, the sensor may be between 75 μm and 500 μm. In some embodiments, the sensor may be between 100 μm and 250 μm.

In some embodiments, the reflector layer 104 may have a patterned shape. The patterned shape may allow a center secondary aperture 118 through which light may pass through with a minimum of interference, such as for a person to see through. The reflector layer 104 may have a plurality of other secondary apertures 118 that may increase the flexibility of the reflector layer 104. In some embodiments, the reflector layer 104 may be shaped like a ring, with a plurality of secondary apertures 118 cut into the ring, so the ring has a center aperture 116 for a person or animal to see out of, and one or more smaller secondary apertures 118. As an analogy, the reflector layer 104 may resemble a rotary phone dial, without the center, and having the secondary apertures 118 spaced along the entire perimeter. In some embodiments, the secondary apertures 118 may be spaced such that there may be a wider amount of the reflector layer 104 between the secondary apertures 118 than is shown. In some embodiments, the secondary apertures 118 may be grouped in symmetrical or asymmetrical groupings along the perimeter of the reflector layer 104. In some embodiments, the material between each secondary aperture 118 may form a strut 120 or other connector between the secondary apertures 118. These struts 120 may be thin enough that they may be flexible under load, such as changes in the IOP of the eye. The struts 120 may concentrate the stress loads of the circular portion of the PECL into the struts 120, as there may be less material overall to distribute the stress to in the presence of the secondary apertures 118. Thus each secondary aperture 118 may help increase the stress load experienced by the struts 120 as compared to the PECL without secondary apertures.

In some embodiments, the cut outs arranged along with ring of the PECL may be circular. In some embodiments the cut outs may be oval or oblong shaped. In some embodiments the cut outs may be uniform cut outs, or they may vary individually. In some embodiments there may be alternating designs of the cut outs.

In some embodiments, the reflector layer 104 may be sandwiched between the base layer 102 and the photoelastic layer 106. The photoelastic layer 106 may have a plurality of cut outs 110 that may correspond to the position of the secondary apertures 118. The matching position of the cut outs 110 in the photoelastic layer 106 and the secondary apertures 118 may allow the PECL to exhibit strain related response at the positions of maximally concentrated stress. The various cut outs 110 may be filled with hydrogel when the top layer 108 may be placed on top of the assembly. In some embodiments the cut outs 110 may be filled with a different material having similar characteristics to hydrogel.

Figure 2:
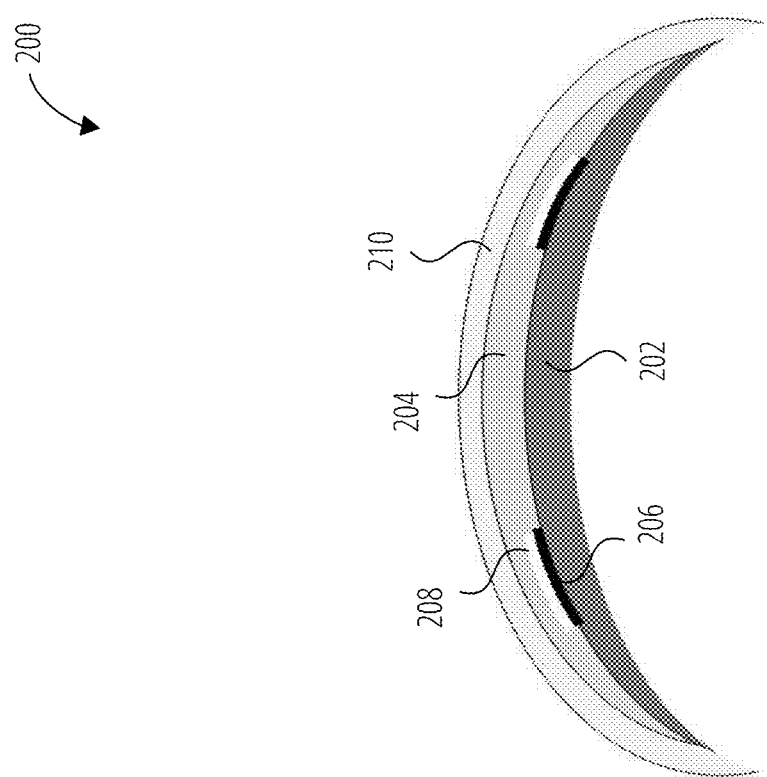
FIG. 2 illustrates a cross section vie of a PECL 200 in accordance with an embodiment.
Figure 3:
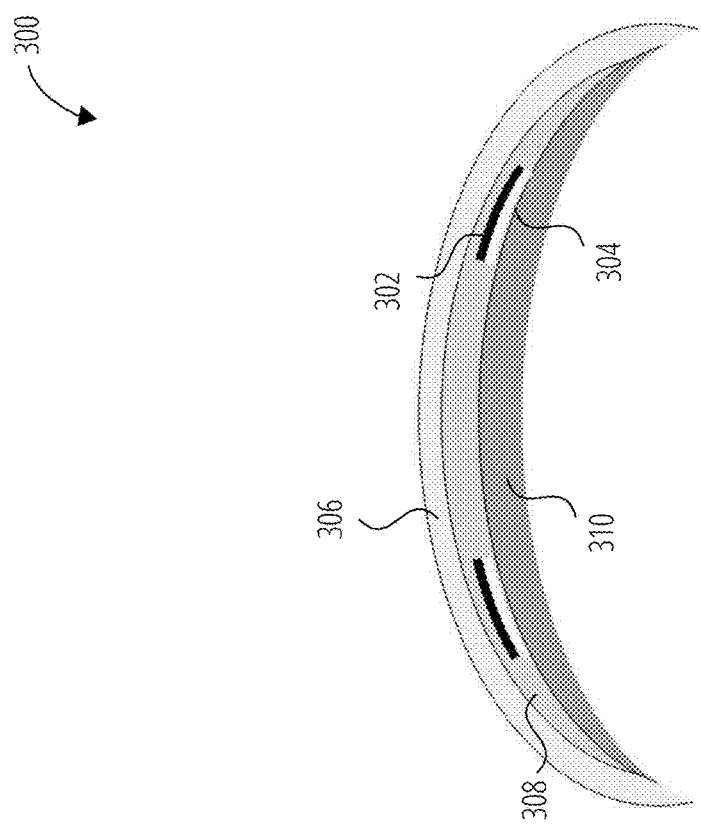
FIG. 3 illustrates an alternative cross section of a PECL 300 in accordance with an embodiment.

In some embodiments, the PECL 200 may include a cavity 208 that may be positioned above the reflector layer 206 as shown in FIG. 2. The cavity 208 may be any shape and size relative to the reflector layer 206 and/or the struts. The cavity 208 may be formed or cut into the photoelastic layer 204. In some embodiments, the cavity 208 may be cut into the base layer 202 so that the cavity is below the reflector layer 206. The cavity 208 may be air filled, or filled with a specialty gas, gas mixture or liquid material. In some embodiments, the cavity 208 may amplify the in-plane stress in the base layer 202 when there are changes to the corneal radius due to changes in the intraocular pressure of the eye.

In some embodiments, the PECL 300 may have a base layer 310, photoelastic layer 308 and hydrogel layer 306 as previously described. The reflector 302 may be positioned on top of the cavity 304, so that the gas filled cavity 304 may be below the reflector 302. In some embodiments, the cavity 304 and the reflector 302 may both be incorporated into the photoelastic layer 308. In some embodiments, the cavity 304 may be incorporated into the base layer 310.

Figure 4:
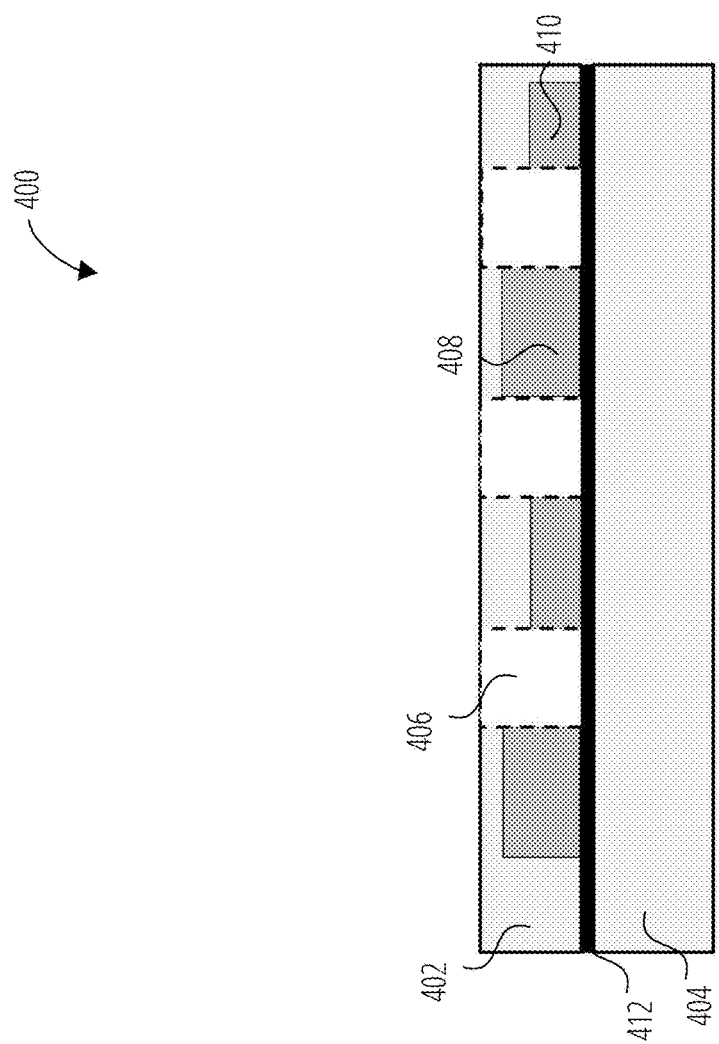
FIG. 4 illustrates a sample cross section of PECL 400 in accordance with an embodiment.

A cross section of a portion of the layers in a PECL device 400 is shown according to an embodiment. Referring now to FIG. 4, the photoelastic contact lens may have a top elastomeric layer 402 and a bottom elastomeric layer 404. A reflector 412 may separate the two layers, or the two layers may be formed directly one on top of the other. In an embodiment, the top elastomeric layer 402 may have one or more various stress concentration feature hole 406 separating a thick photoelastic layer 408 and a thin photoelastic layer 410. In some embodiments, the thick and thin photoelastic layers may be alternating. In some embodiments, the thick photoelastic layer 408 may be adjacent to another thick photoelastic layer 408 (not shown), or a thin photoelastic layer 410 may be adjacent to another thin photoelastic layer 410. The variations of the thick or thin photoelastic layers may be used in different patients, where different IOP readings may be anticipated. In some embodiments, some subjects that may benefit from the present disclosure may not be human, and the eye characteristics may be such that the use of thin and think photoelastic layers may require modification in position, orientation or frequency to maximize effectiveness. In some embodiments, patients may suffer from other disorders that may affect their eyes or their vision, requiring modifications to the structure and design of the sensor described herein.

In some embodiments, the photoelastic regions may have varying thicknesses at different locations along the cross section. The benefit of such a non-uniform thickness may be having different overall polarization rotations at the different regions, thereby allowing the use of one thickness as a reference region. Such a self-referenced measurement may have the benefit of eliminating the reflection signals coming from the front surface of the PECL and providing a more accurate measurement. In some embodiments, the holes between the different regions can be eliminated, and interchanging high and low thickness regions can be stacked along the device. The benefit of such an arrangement may be the elimination of contrast in the reflected light when there is no strain, and appearance of contrast only when there is a strain due to IOP changes. Such a self-referenced optical measurement also eliminates non-strain related optical reflections and allow more accurate remote optical measurements.

Figure 5:
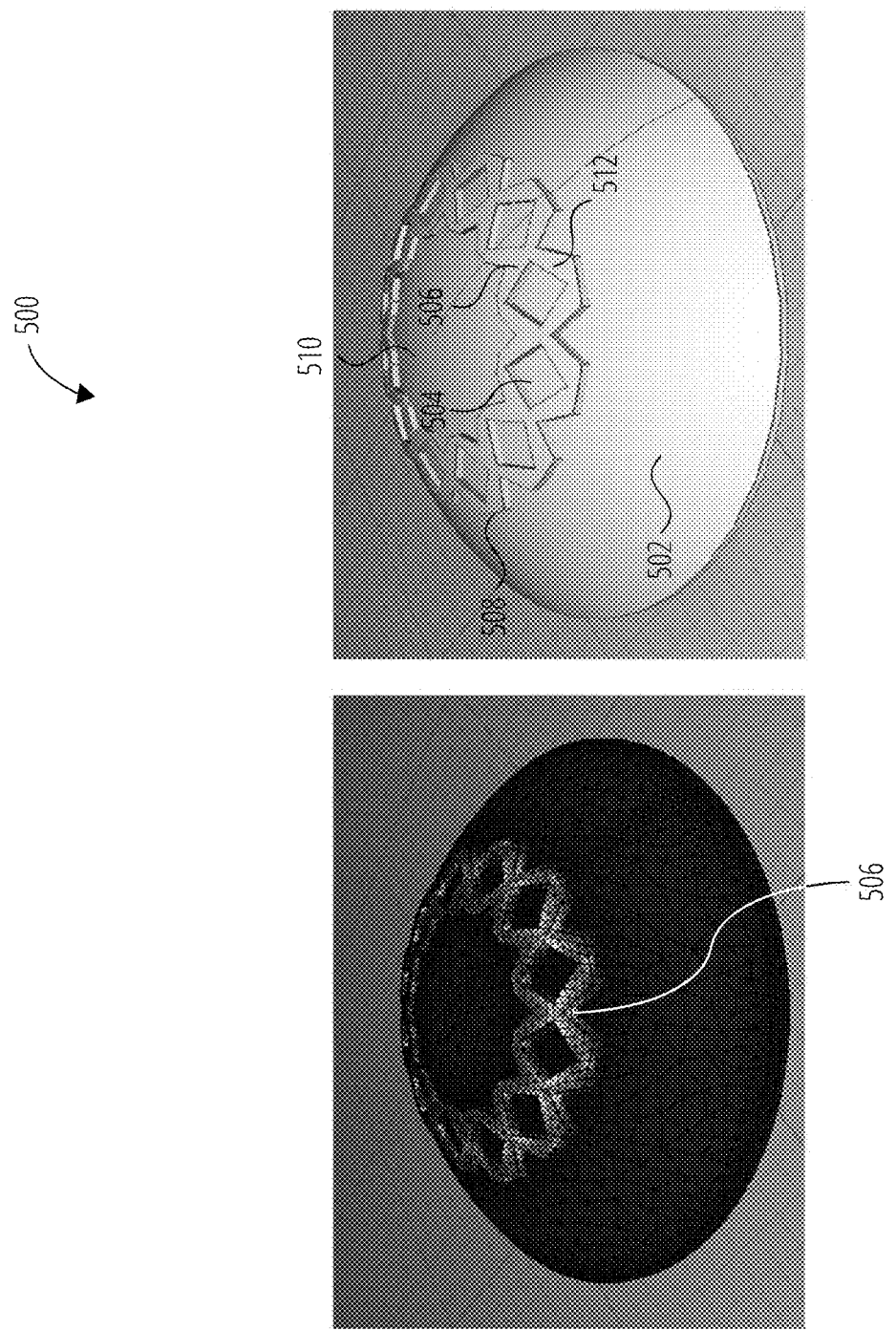
FIG. 5 illustrates a comparison of a sample stress load calculated under two different loads 500 in accordance with an embodiment.

In some embodiments, the aperture cut outs 504 in the reflector layer 508 may be generally square shaped, as shown in FIG. 5. The partially assembled PECL 500 may have a base layer 502 and a reflector layer 508. The reflector layer 508 may have square shaped aperture cut outs 504. The center aperture 510 may be large enough so the reflector layer 508 does not interfere with the field of view of the eye. The boundary of the center aperture 510 need not be uniform or circular, as shown. In some embodiments, the struts 512 may connect at intersections. The strut intersections 506 may serve as stress concentration points. The image on the left of FIG. 5 illustrations the stress distribution in the lighter shaded area, which may be seen as generally focused in the strut intersections 506. The corners of the square shaped cut outs 504 represent triangle shaped areas of the reflector layer 508. The stress concentration points lie between the triangles and amplify the stress to about 10 MPa when about 15 mm Hg pressure is applied to the base layer 502.

Figure 6:
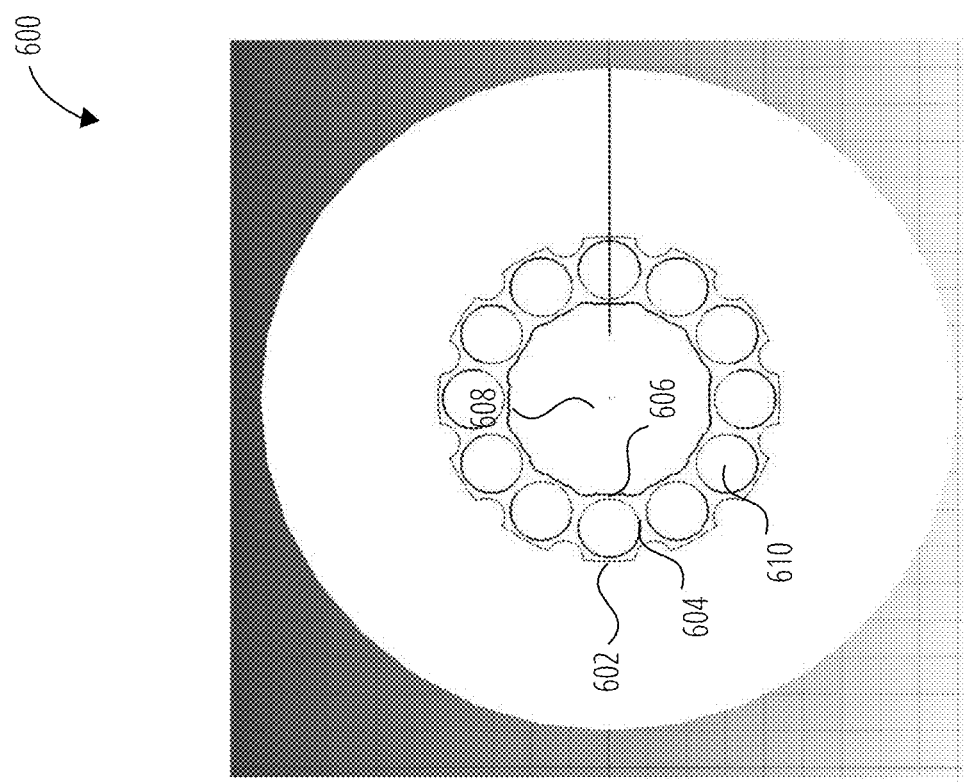
FIG. 6 illustrates a stress sensor 600 in accordance with an embodiment.

In some embodiments, the stress sensor (photoelastic layer and reflector layer) may take a variety of forms. In an embodiment, the reflector layer may have a generally flat donut shape, with a series of cut outs made into the donut ring, as shown in FIG. 6. A plurality of cut outs 610 remove material from the reflector layer, and create bands of material connecting and generally maintaining the shape of the reflector layer. The individual cut out 610 may have an outer edge 602, an inner edge 606 and a strut 604 on each side. In some embodiments, one or more of the outer edge 602, inner edge 606 and strut 604 may serve as a stress concentration area or volume (referred generally herein as a stress concentration point). A stress concentration point may amplify the stress when pressure is applied to the base layer, and subsequently the pressure may be distributed throughout the PECL device.

Figure 7:
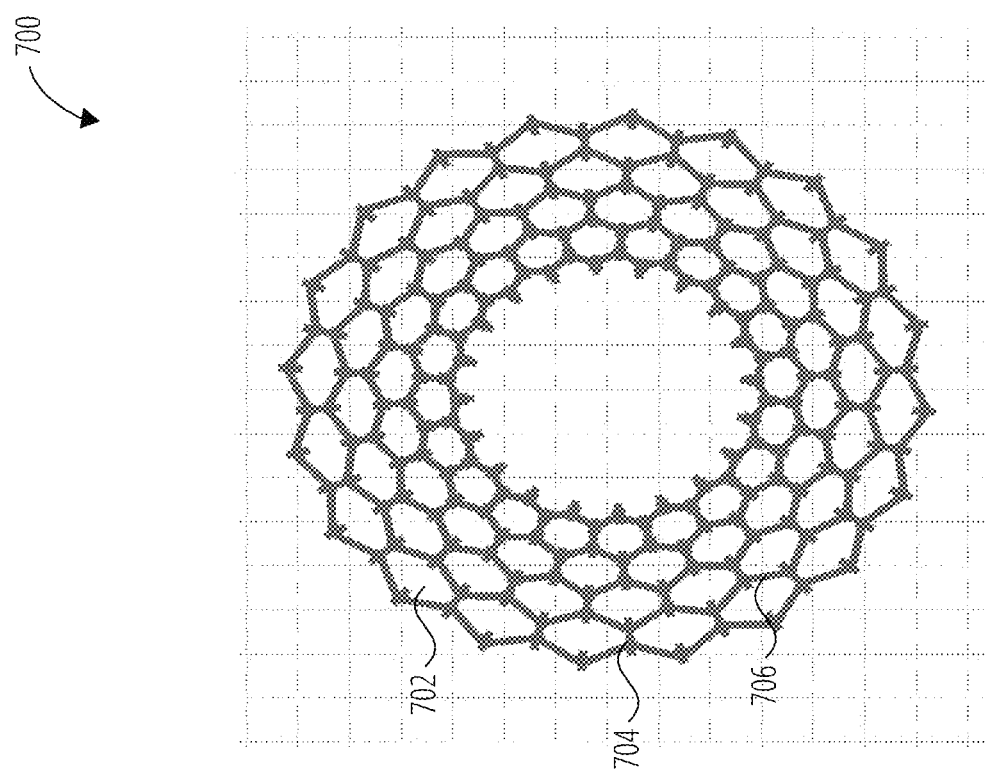
FIG. 7 illustrates a stress sensor 700 in accordance with an embodiment.

In some embodiments, the reflector layer may have a mesh structure, as shown in FIG. 7. The individual struts throughout the entire mesh structure may serve as stress concentration points and amplify the stress when pressure is applied to the base layer (not shown). In some embodiments, the individual cut outs or individual apertures 702 may focus the stress of the aperture area through an edge strut 706 or a radial strut 704. The struts may have any orientation, and the aperture may be any size and shape.

In some embodiments, the measurement of IOP may come from one stress concentration area. In some embodiments the IOP calculation may be made using several stress concentration areas. In some embodiments, every stress concentration area may be used to determine the IOP value.

Figure 8:
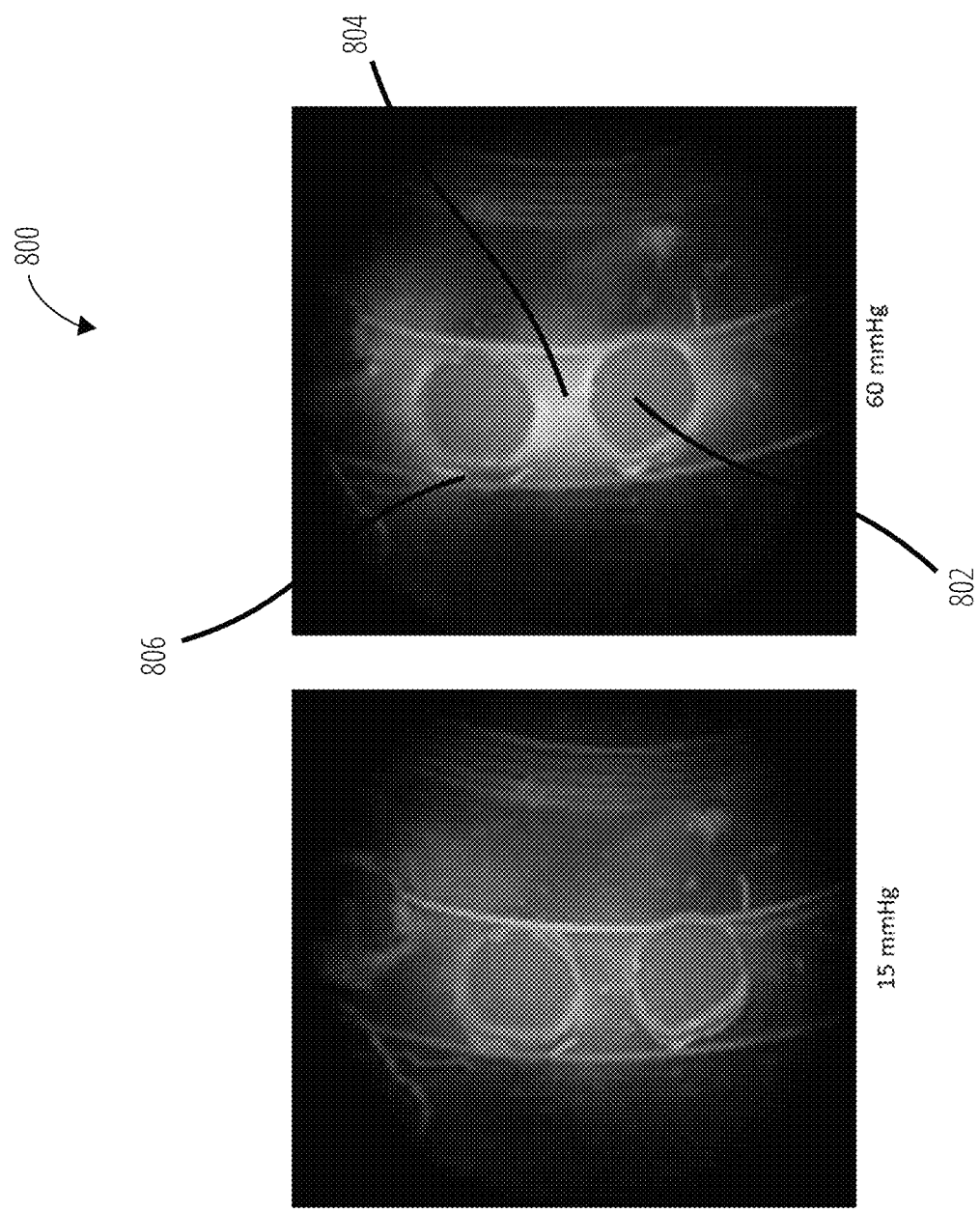
FIG. 8 illustrates the reflected light measures from a sensor placed on an eye model at two different pressure loads 800 in accordance with an embodiment.

An example of measuring stress using the PECL device is now shown in FIG. 8. Here two images are presented side by side, with the photoelastic response of the device measured in a transmission mode using a circularly polarized illumination from the bottom and an analyzer in front of a camera. The left figure represents an IOP value of about 15 mm Hg and the image on the right represents an IOP pressure of about 60 mm Hg. The changes in measured light intensity between the two images may be observed as a function of induced stress in the PECL. The change in light intensity may be more noticeable in the strut 804 between the cut out 802 apertures. Some amount of stress may also be readable in the outer edge 806.

Figure 9:
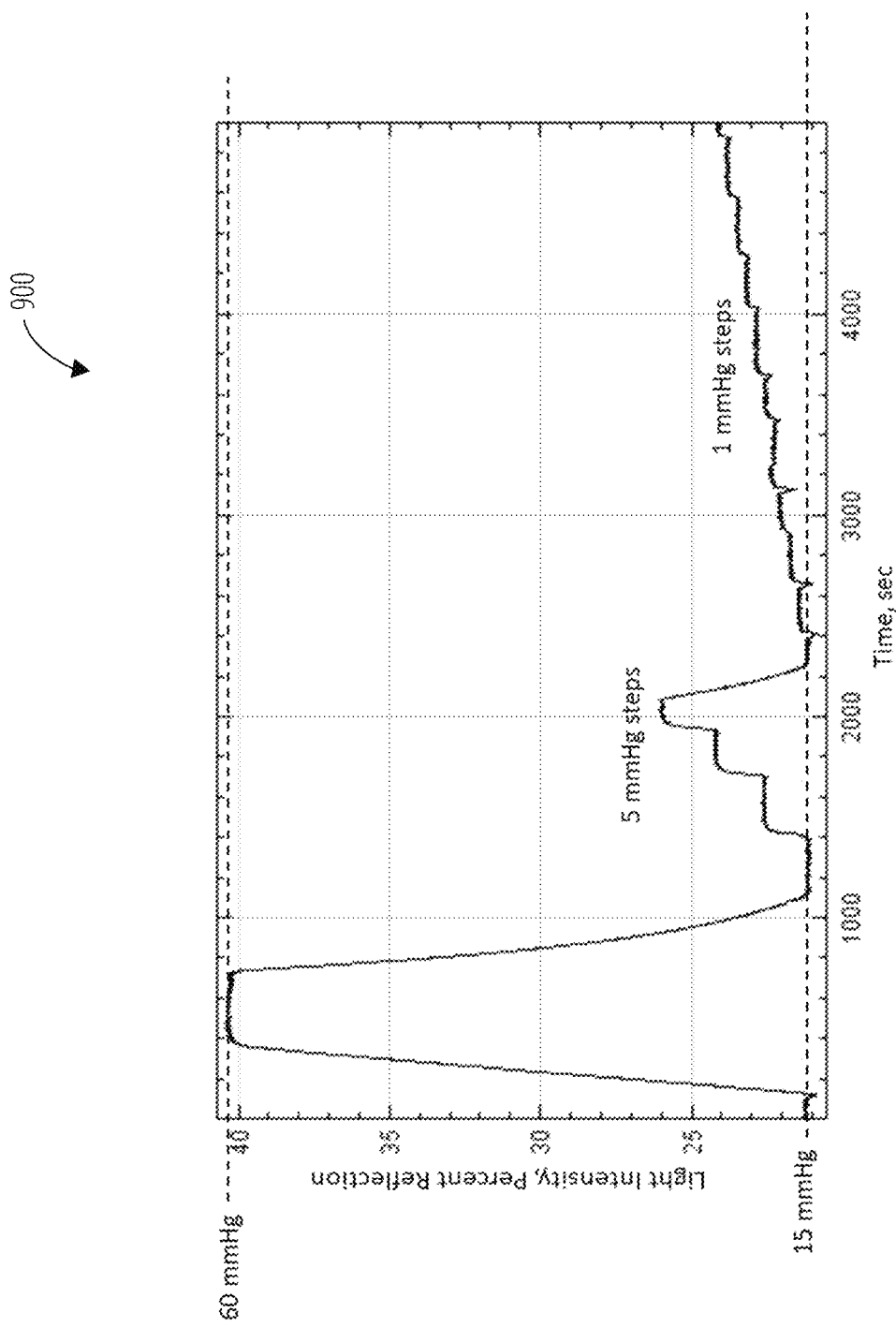
FIG. 9 illustrates a light intensity measured between holes vs load graph 900 in accordance with an embodiment.

In another embodiment, a time series plot 900 of the intensity of the transmitted light extracted from the measurements of FIG. 8 are now shown in FIG. 9. In an embodiment, pressure may be applied to the eye model, and the intensity may change in a linear fashion. Small steps of down to 1 mm Hg may be resolved from single region of interests (ROIs) with a signal-to-noise ratio of about 5 with 30 msec acquisition time. The graph shows intensity of reflected light in percentage of full scale as the pressure applied to the eye-model may change stepwise from 15 mm Hg to 60 mm Hg and back to 15 mm Hg (between 100 sec and 700 sec), from 15 mm Hg to 30 mm Hg in 5 mm Hg steps and back to 15 mm Hg in a single step (between 1200 sec to 2100 sec), from 15 mm Hg to 25 mm Hg with 1 mm Hg steps (starting at 2200 sec). By measuring the percent reflection, the graph can be used to infer the IOP level using a multiplication factor, as the sensor may be linear. The detectable pressure difference may be about 0.2 mm Hg in real time with 30 frames per second (FPS) image rate.

The graph shown in FIG. 9 illustrates a laboratory measurement over the course of whole seconds (the unit of the X axis). In operation the polarimetric measuring device may take pictures and analyze them in milliseconds, making use of video camera or still image capture of a polariscope or a camera on a mobile device.

Figure 10:
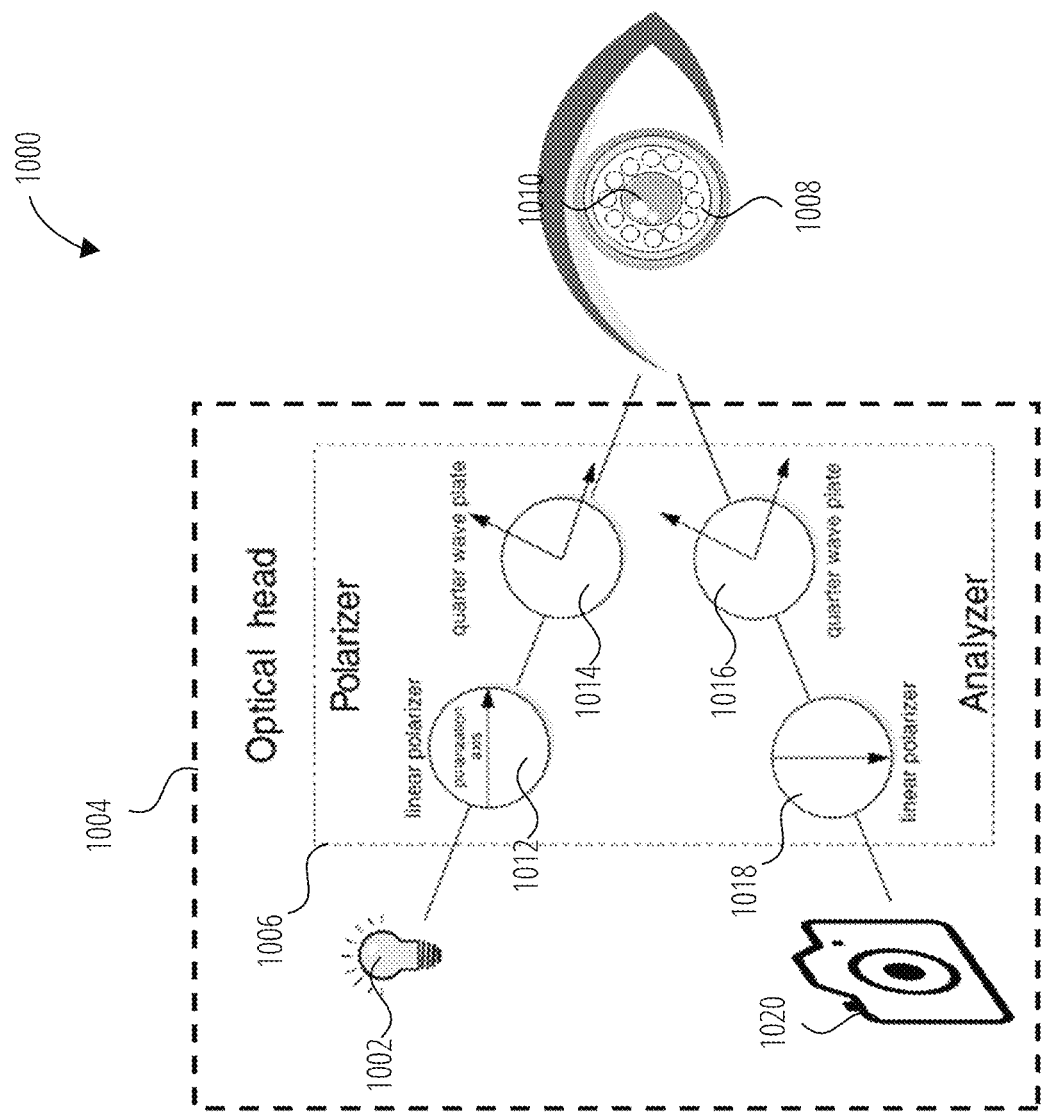
FIG. 10 illustrates a sample polarimetric measuring device 1000 in accordance with an embodiment.
Figure 11:
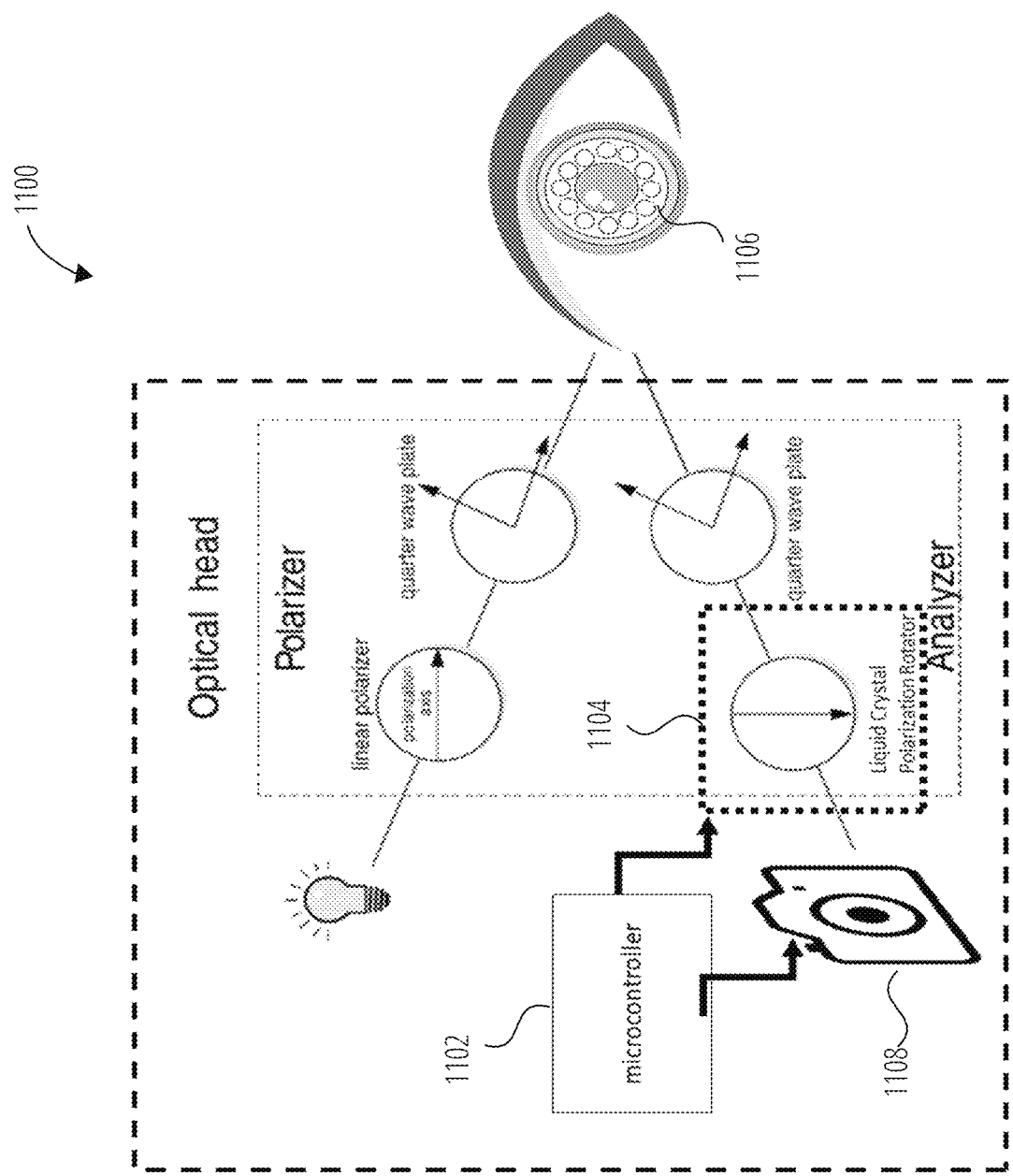
FIG. 11 illustrates a sample polarimetric measuring device 1100 in accordance with an embodiment.

In some embodiments, a polariscope 1000 may be used to measure the reflectance of the PECL device, as shown in FIG. 10. An illuminator with a polarizer casts illumination on the sample device, and the reflected light may be imaged through an analyzer with a camera. In some embodiments, the polariscope may be an optical head 1004 with a a light source 1002. The light source 1002 emits light toward a polarizer 1006. In some embodiments, the polarizer may have a linear polarizer 1012 and a quarter wave plate 1014 in the path of the light source 1002 to the pupil 1010. Then a set of reflective polarizers for the light reflected off the PECL 1008 device. These polarizers may again be a quarter wave plate 1016 and a linear polarizer 1018. In some embodiments, the reflected linear polarizer 1018 may have the axis of polarization offset from the transmission linear polarizer 1012 by 90 degrees. The light that passes through the reflector polarizers 1016, 1018 may then be detected and imaged using a camera 1020.

In some embodiments, there may be a polarimetric measuring device, which may be an attachment device for connecting to a mobile device such as a cell phone. In some embodiments, the attachment device may have a built in light source, such as a LED light engine. In some embodiments, the attachment device may have a camera. In some embodiments the attachment device may utilize a camera built into the mobile device, and use a software program (App) to control the mobile device and attachment device for determining measurements from the PECL 1008. In some embodiments the PECL may be a PEIOL.

In some embodiments, an illuminator with a polarizer, may cast illumination on the sample PECL 1106 device, and the reflected light may be imaged through an analyzer 1104 controlled by a microcontroller 1102, and images taken with a timed camera 1108.

In some embodiments, an illuminator that has a narrow-band computer-controlled light with a polarizer may cast illumination on the sample PECL device. The reflected light may be imaged through a computer-controlled analyzer. The reflected light may pass through a narrowband optical filter and be imaged with a timed camera 1108. In some embodiments the light may be filtered using mechanical optical filters to produce a particular polarization of a light source.

Figure 12:
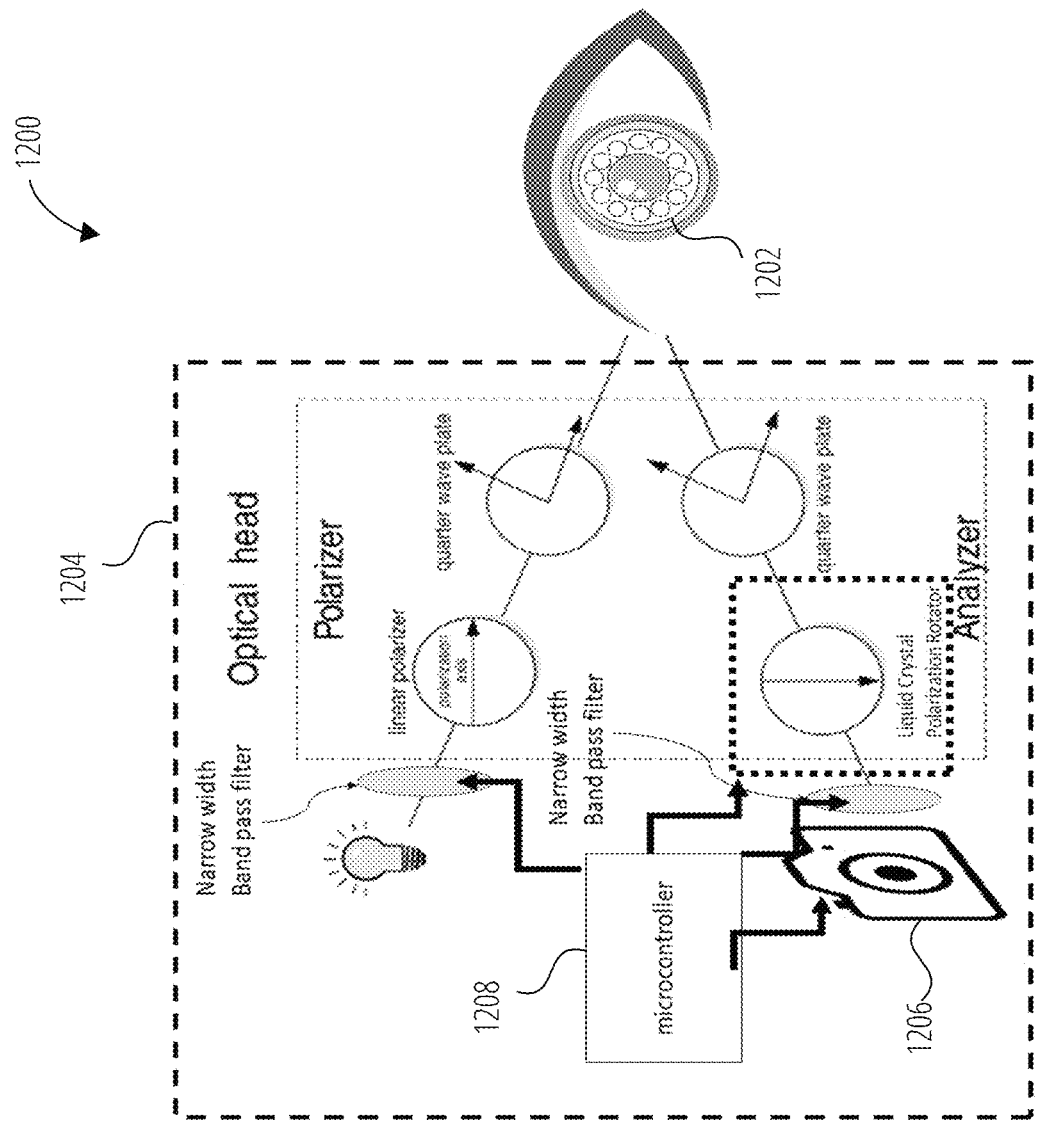
FIG. 12 illustrates a sample polarimetric measuring device 1200 in accordance with an embodiment.

In some embodiments, the PECL 1202 may be read using a polarimetric measuring device 1204 as shown in FIG. 12. The polarimetric measuring device 1204 may have a body combining a light source, various polarizing filters, and one or more narrow width band pass filters as shown. The polarimetric measuring device 1204 may include a camera 1206 or may rely on a camera in a mobile device (not shown). The camera and one or more various analyzers in the polarimetric measuring device 1204 may utilize a common computer processor 1208, such as a micro controller in the polarimetric measuring device 1204, or in the mobile device.

In some embodiments, the polarimeter measuring device may produce the proper polarized light every few milliseconds. A mobile device app may control the polarimeter measuring device and the camera of a mobile device to properly synchronize the production of the light and the taking of an image to record the reflected light.

Figure 13:
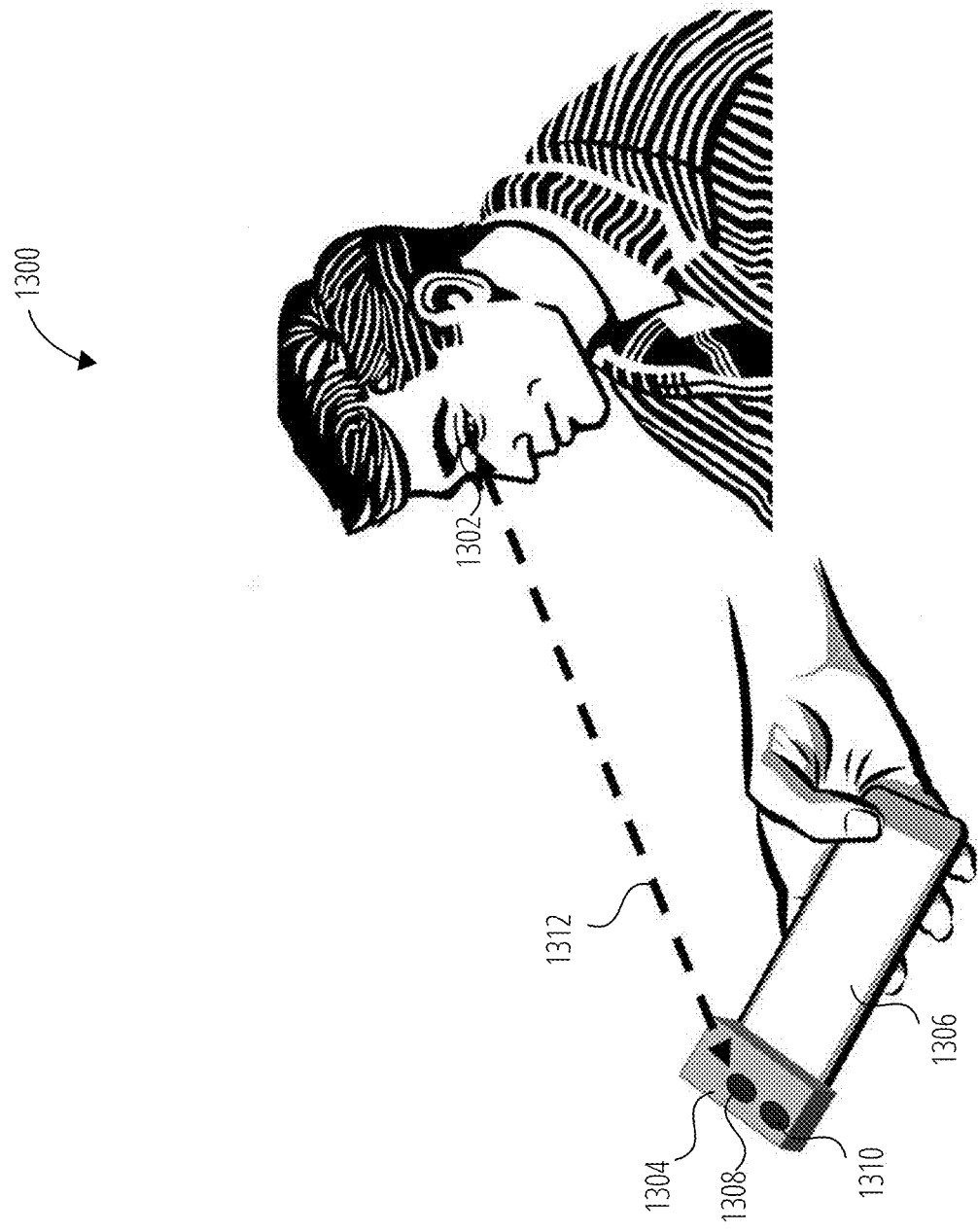
FIG. 13 illustrates an optical head connected to a mobile device 1300 in accordance with an embodiment.
Figure 14:
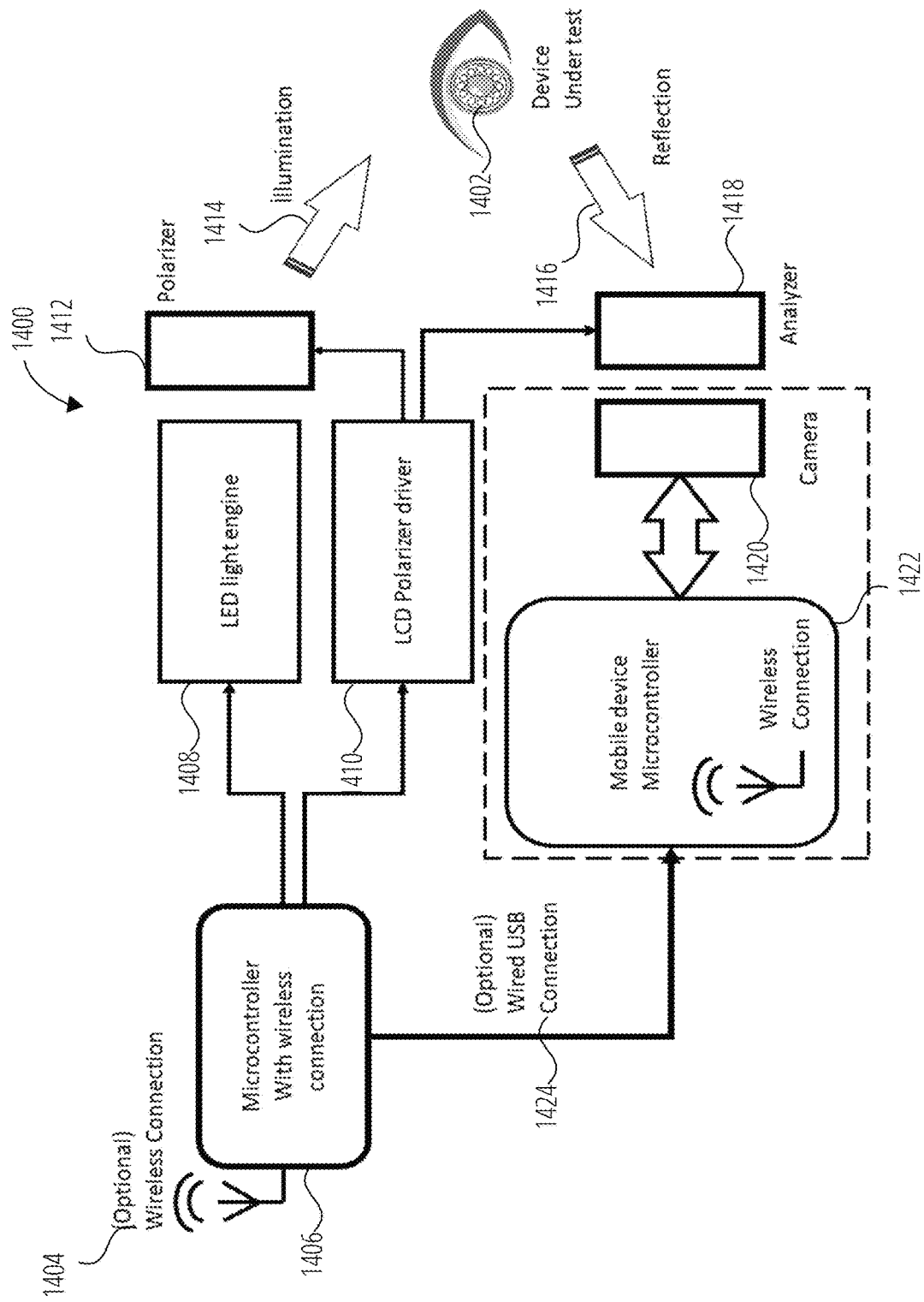
FIG. 14 illustrates a function diagram of a system 1400 in accordance with an embodiment.

In some embodiments, a polariscope 1304 may be a consumer electronic device. The consumer electronic device may be a cell phone attachment, a standalone device, or a program (app) for use in a cell phone or other consumer electronic, as shown in FIG. 13. In some embodiments, there may be a polarimetric measuring device (PMD). The polarimetric measuring device may have a body, and a circuit contained within the body. The circuit may have a micro controller, an analyzer and an interface connector. The polarimetric measuring device may also have a light source in electrical communication with the circuit. The light source may have a variable output which may be adjusted through the circuit, or a software program controlling the circuit, or controlling the light source. The PMD may have a polarizer with a retarding plate. The retarding plate may condition the output of the light source to produce a particular polarization. In some embodiments, the PMD may also have a camera.

In some embodiments, the polariscope 1304 may be an attachment to a mobile device 1306, such as a cell phone. The polariscope 1304 may use a high resolution front side camera 1308 for image capture. The polariscope 1304 may have a wavelength controlled illuminator 1310. Polarization filter and wavelength-controlled illuminator may be embedded into the attachment. The attachment may be controlled by software on the mobile device 1306. The polariscope 1304 may project light at the PECL device 1302, and read the reflected light in order to determine any IOP change in the eye. The user may look directly into the front side camera 1308 and the wavelength-controlled illuminator 1310 along a line of vision 1312. The polariscope 1304 may use one or more scannable elements on the PECL device 1302 to determine if the line of vision 1312 is correct. Once the line of vision 1312 is determined to be correct, the PECL device 1302 may automatically begin scanning the PECL device 1302 to get a reading on the IOP of the eye. In some embodiments, the scan may be manually triggered, or triggered by some other means.

In some embodiments, the mobile device may have access to the cloud, either through a local WIFI or other short-range wireless system, or via using a cellular RF network. If the mobile device 1306 with the polariscope 1304 are connected to the cloud, the PECL device 1302 may be read remotely by a physician or other health care provider.

In some embodiments, the PECL device 1302 (which may alternatively be a PEIOL device), may be used with the mobile device 1306 and the polariscope 1304 (PMD) to form a system for determining the IOP of an eye. The system may have a deformable sensor suitable for placement on or in the eye. The sensor may have one or more stress features related to a photoelastic material. The sensor may be in a biocompatible body. The system may also have a polarimetric measuring device (PMD) that has a light source and one or more polarizing filters. The PMD may be capable of producing polarized light. The system may use a mobile computer device, such as a cell phone, table or laptop computer. The mobile device may operate a software program for capturing an image via a camera (the camera may be part of the mobile device or part of the PMD). The image may be produced from the reflection of polarized light off the sensor. The reflected light may pass through an additional polarization filter before being captured by an image sensor. In some embodiments, the PMD may have physical or electronic polarizing filters. In some embodiments, the PMD may have filters that may be interposed between the mobile device camera and the sensor, so reflected light may pass through one or more filters of the PMD before the image is captured.

In some embodiments, the PECL or PEIOL device may be part of a system 1400. The system 1400 may encompass the PECL 1402 (or PEIOL) device along with a mobile device 1422 and a portable polariscope, shown as having a microcontroller 1406, LED light engine 1408, LCD polarizer driver 1410, Polarizer 1412, analyzer 1418 and camera 1420. In some embodiments, a remote signal may be received via a wireless connection 1404. The connection may activate the polariscope or prompt a user to use the polariscope to measure a person's IOP. The prompt may be through the polariscope or through the mobile device 1422. The user may attach the polariscope to a mobile device, or the mobile device may have a polariscope built into it. The user may activate an app or other program that may control the polariscope. The user may align their eye, and the PECL 1402 with the camera 1420. Then the microcontroller 1406 may activate the LED light engine 1408 and the LCD polarizer driver 1410 to emit light through a polarizer 1412 and at the PECL 1402 device. In some embodiments, the LED light engine 1408 may have sufficient capabilities so that the LCD polarizer driver 1410 or the polarizer 1412 may not be needed. The light reflects off the PECL 1402 in the form of reflection 1416 image and may pass through an analyzer 1418 before being captured in a camera 1420. The camera 1420 creates an image which may then be analyzed by the mobile device 1422 according to an algorithm or program to convert the image into IOP data.

Figure 15:
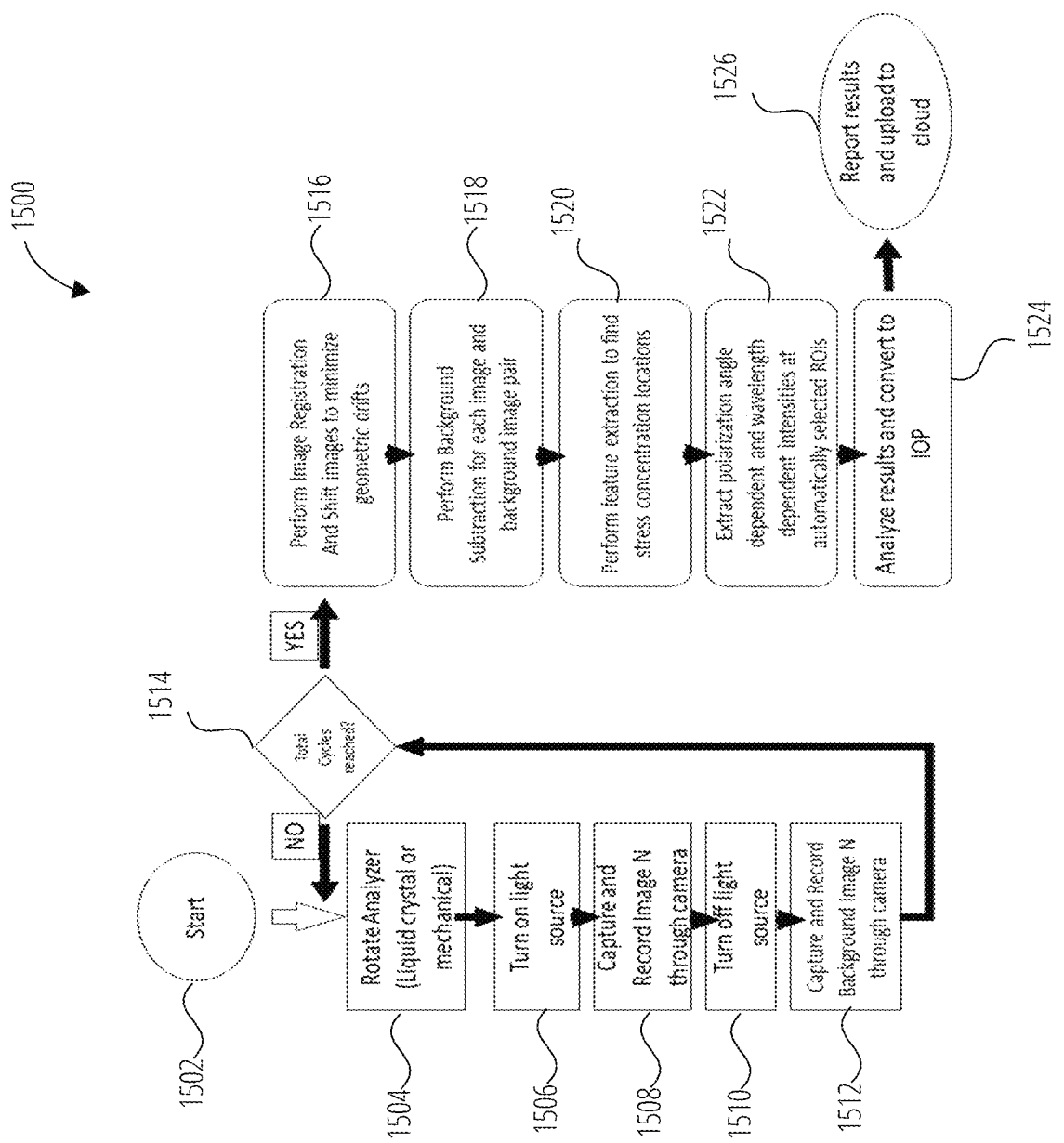
FIG. 15 illustrates a flow chart of an analytical process 1500 in accordance with an embodiment.

In some embodiments, there may be a process for determining the IOP change measured from a PECL device, as shown in FIG. 15. The process may be designed to compensate for, or reduce background optical effects, such as reflections and ambient illumination. The process may still allow for accurate determination of IOP readings. In some embodiments, optical images from the PECL device on the cornea may be acquired in succession. The illumination may be turned on and off while the polarization is electronically rotated during analysis. The captured images may then be used in image processing algorithms to remove background and geometric drifts, while intensity changes may be extracted using built in reference locations on the PECL device. The data may then be used to infer the IOP value, which may then be reported to the user through their mobile device or reported to the cloud.

In some embodiments, the process may begin at start block 1502 when a user may activate the program or app by loading the app in their mobile device. The process may begin with rotate analyzer 1504, which may be a liquid crystal, mechanical or electrical. A light 1506 may be activated. The light may be part of the mobile device, or it may be a light built into the polariscope used as an attachment to a mobile device. The process may then do one or more image capture 1508 steps and record the image(s) with a camera built into the polariscope or the mobile device. The light is turned off (light off 1510) and one or more additional images may be used to capture background 1512 images with the camera. The program may evaluate total cycles 1214 to determine if enough data has been gathered to perform an IOP calculation. If not enough data has been gathered, the process returns to the rotate analyzer 1504 step. If enough data has been captured, the process moves on to do image registration 1516. In image registration 1516, the device may shift the captured images to minimize geometric drift. Background subtraction 1518 may be done on each image and each image pair (image captured with light on, and background image captured with light off). A feature extraction may be done to identify stress concentration 1520 in the stress concentration areas. The process may then determine polarization angle 1522 and wavelength dependent intensities at automatically selected regions of interest (ROI). The process may then analyze the results and convert data to IOP information 1224. The IOP data may then be reported (report IOP 1526), which may appear on the mobile device or be transmitted to the cloud. In some embodiments, the mobile device may be physically connected to a computer, and the data transferred through a cable.

In some embodiments, an image may be captured every few milliseconds. In some embodiments the images may be captured with about 100 msec delay between each image. In some embodiments, the camera may capture a video image of the reflected light, with an analysis performed on the appropriate video frame corresponding to the timing of an image desired at a particular time. The app may parse the video into discreet frames for the analysis.

Figure 16:
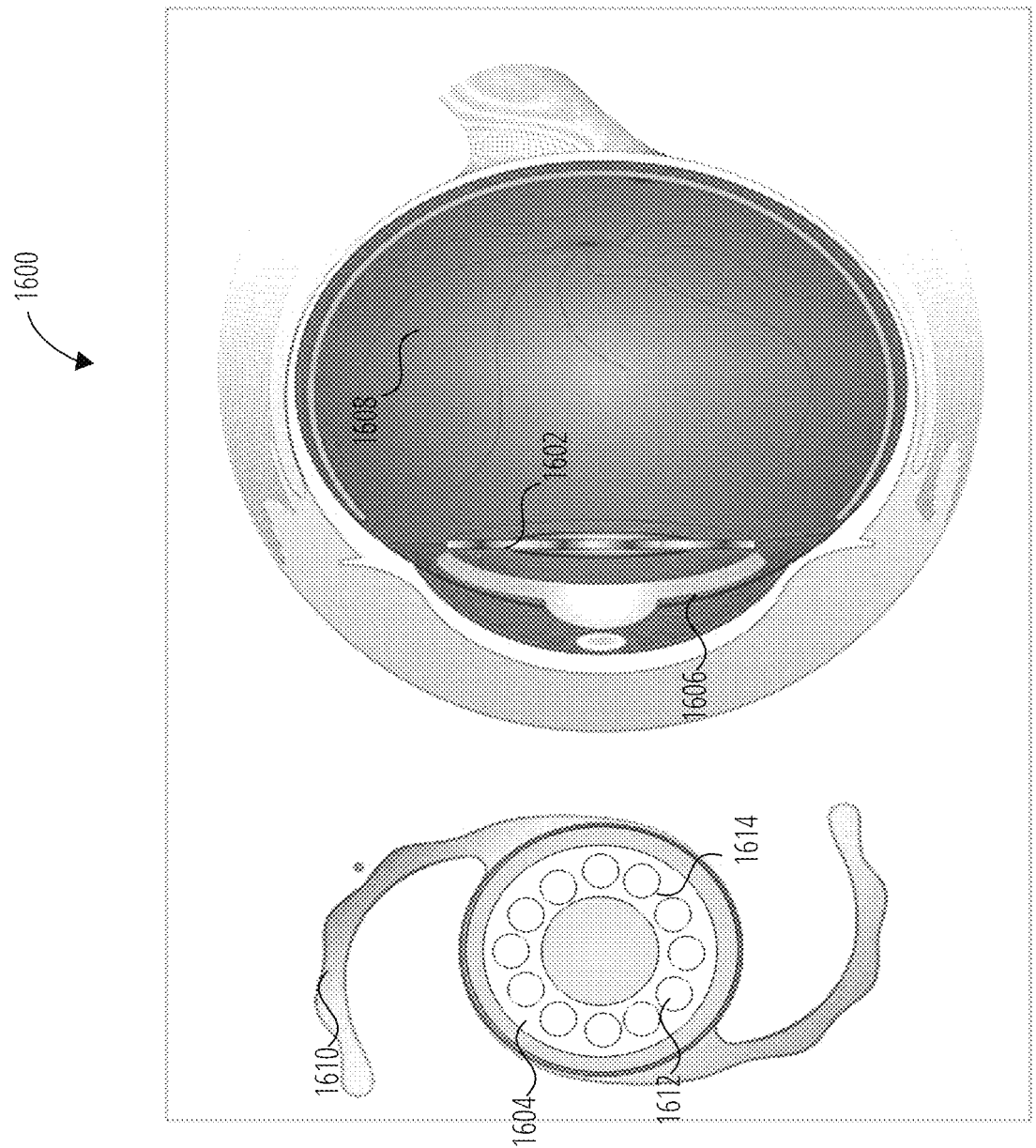
FIG. 16 illustrates a photoelastic intraocular lens (PEIOL) 1600 in accordance with an embodiment.

In some embodiments there may be a photoelastic intraocular lens (PEIOL) form of the device, as shown in FIG. 16. In some embodiments, there may be a sensor device for measuring intraocular pressure (IOP) in the form of an implantable lens. The implantable lens may have a body composed of a biocompatible elastomeric material. The body may be configured to fit inside an eye. The body may have a first support leg, which may extend radially from the body. The sensor may have a photoelastic layer having a center aperture and a plurality of secondary apertures. The secondary apertures define a set of struts, and the struts may operate as stress concentration features. The photoelastic layer may be embedded in the body. The sensor may have a reflector layer with a foot print that substantially matches the foot print of the photoelastic layer. The reflector layer may be adjacent to the photoelastic layer. A gas filled cavity may be adjacent to either the photoelastic layer or the reflector layer. In operation, chances in the intraocular pressure may cause the body to deform. The deformation of the body may stress the photoelastic layer and produce an optical result.

In an embodiment, the PEIOL 1602 device is shown implanted into an eye 1608 on the right side of FIG. 16. The PEIOL may be implanted under the natural lens 1606 in the eye. On the left side of FIG. 16, a plan view of the PEIOL device may be seen. The PEIOL may have one or more implantation legs 1610, which may help to secure the PEIOL 1602 in place and prevent the PEIOL 1602 from movement within the eye 1608. The PEIOL may have similar structural elements to the PECL device with a reflector layer 1604 having a plurality of cut out 1612 apertures with struts 1614 between each aperture. The struts may operate in a similar fashion to focus stress on them when pressure in the eye is exerted on to the PEIOL 1602 device.

In some embodiments, the PEIOL device may be between 2 μm to 1000 μm thick. In some embodiments the PEIOL may be between 75 μm and 700 μm. In some embodiments the PEIOL may be between 125 μm and 300 μm.

Figure 17:
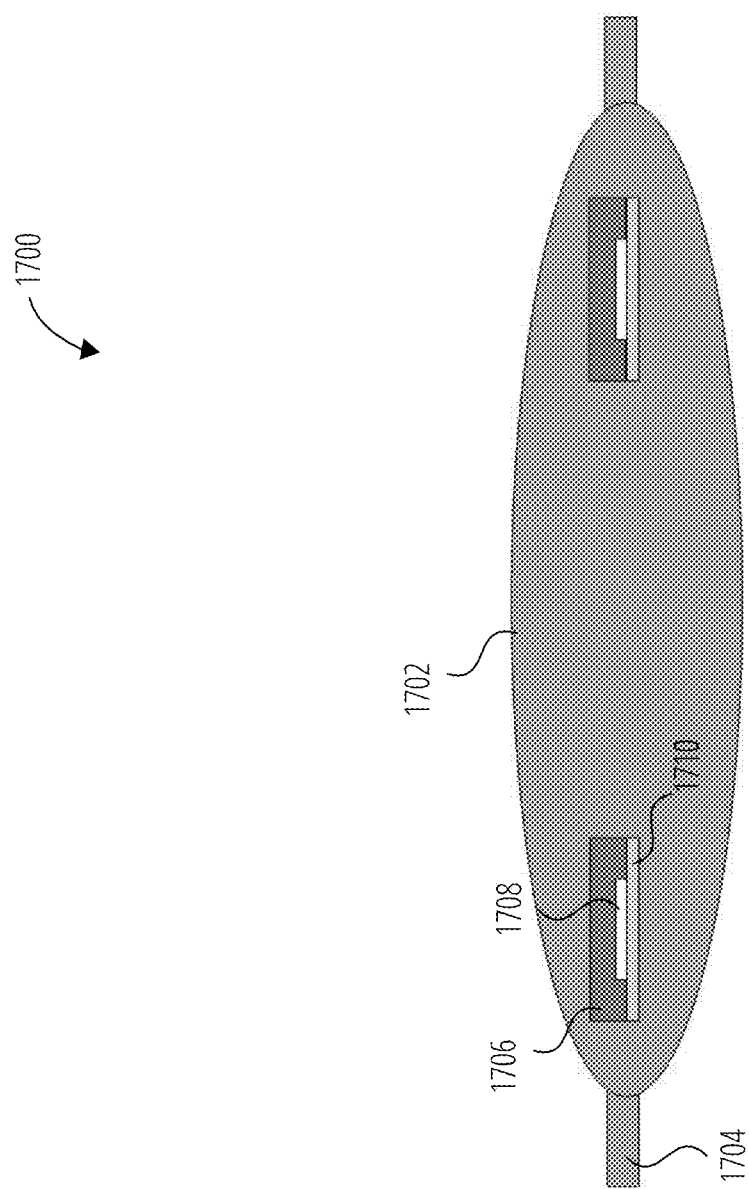
FIG. 17 illustrates a cross section of a PEIOL 1700 in accordance with an embodiment.
Figure 18:
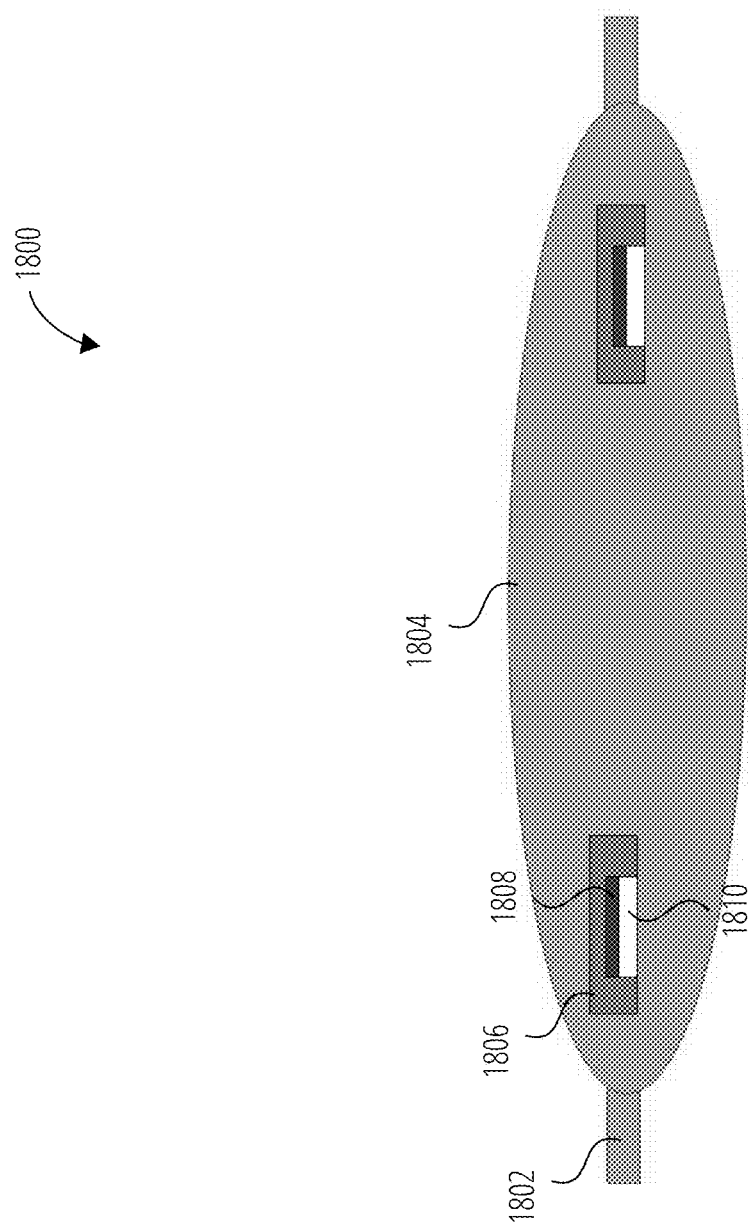
FIG. 18 illustrates a cross section of a PEIOL 1800 in accordance with an embodiment.

In some embodiments, the IOP sensing device may take the form of an intraocular lens (PEIOL) device, as shown in FIG. 17. The PEIOL device 1700 may have an elastomeric body 1702 with one or more implantation leg 1704 extensions. The implantation leg 1704 may help stabilize or anchor the PEIOL inside the patient eye. The photoelastic sensor region may have a photoelastic layer 1706 with a cavity 1708 and a reflector 1710. The assembly of the photoelastic layer 1706, cavity 1708 and reflector 1710 may be embedded into the elastomeric body 1702. Any IOP changes in the eye may directly modulate the pressure on the cavity and the stress at the top surface may be modulated due to mechanical deformations of the cavity, resulting in a photoelastic response.

In some embodiments, the PEIOL device may have different optical characteristics than the PECL device. Optical sensors used with the PEIOL device may have an automated method of determining whether they are reading a PECL or a PEIOL device. Alternatively, there may be a manual indicator for a user to select or toggle between a PEIOL or a PECL device.

In some embodiments, the PEIOL may have the cavity 1810 positioned below the reflector 1808 and within the photoelastic layer 1806. The photoelastic layer 1806 may be contained within the body 1804. One or more implantation leg 1802 may extend from the body 1804 to anchor the PEIOL device in place within the eye.

Embodiments of the subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer program instructions, encoded on one or more computer storage medium for execution by, or to control the operation of, data processing apparatus, such as a processing circuit. A controller or processing circuit such as CPU may comprise any digital and/or analog circuit components configured to perform the functions described herein, such as a microprocessor, microcontroller, application-specific integrated circuit, programmable logic, etc. Alternatively or in addition, the program instructions may be encoded on an artificially generated propagated signal, e.g., a machine-generated electrical, optical, or electromagnetic signal, that is generated to encode information for transmission to suitable receiver apparatus for execution by a data processing apparatus.

A computer storage medium may be, or be included in, a computer-readable storage device, a computer-readable storage substrate, a random or serial access memory array or device, or a combination of one or more of them. Moreover, while a computer storage medium is not a propagated signal, a computer storage medium may be a source or destination of computer program instructions encoded in an artificially generated propagated signal. The computer storage medium may also be, or be included in, one or more separate components or media (e.g., multiple CDs, disks, or other storage devices). Accordingly, the computer storage medium is both tangible and non-transitory.

The operations described in this specification may be implemented as operations performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations, of the foregoing The apparatus may include special purpose logic circuitry, e.g., an FPGA (field programmable gate array) or an ASIC (application specific integrated circuit). The apparatus may also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment may realize various different computing model infrastructures, such as web services, distributed computing and grid computing infrastructures.

A computer program (also known as a program, software, software application, script, or code) may be written in any form of programming language, including compiled or interpreted languages, declarative or procedural languages, and it may be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the subject matter described in this specification may be implemented on a computer having a display device, e.g., a CRT (cathode ray tube) or LCD (liquid crystal display) monitor, OLED (organic light emitting diode) monitor or other form of display for displaying information to the user and a keyboard and/or a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input. In addition, a computer may interact with a user by sending documents to and receiving documents from a device that is used by the user; for example, by sending web pages to a web browser on a user's client device in response to requests received from the web browser.

While this specification contains many specific embodiment details, these should not be construed as limitations on the scope of any embodiments or of what may be claimed, but rather as descriptions of features specific to particular embodiments. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous. In some embodiments, one or more graphic processing unit(s) (GPU) may be used.

Having described certain embodiments of the methods and systems, it will now become apparent to one of skill in the art that other embodiments incorporating the concepts may be used. It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A device for conforming to a surface contour of an eye, the device comprising:
   a body composed of a biocompatible material and having a shape of a contact lens;
   a stress sensor embedded within the body, the stress sensor comprising:
   an annular ring having a central aperture, and a plurality of secondary apertures arranged around the central aperture, the plurality of secondary apertures defining a plurality of struts, the annular ring being made of a photoelastic material;
   wherein a shape of the annular ring, the central aperture and the plurality of secondary apertures define a foot print of the annular ring; and
   a reflector material layered under the annular ring, the reflector material having substantially the same foot print as the annular ring;
   wherein the plurality of struts of the annular ring are configured to flex in response to changes in the surface contour of the eye.

2. The device of claim 1, wherein the body has a thickness of 2 µm to 1000 µm.

3. The device of claim 1, wherein the reflector material further comprises a plurality of pores.

4. The device of claim 1, wherein the foot prints are irregular.

5. The device of claim 1, wherein the annular ring is a UV curable epoxy.

6. The device of claim 1, wherein the struts are stress concentration features.

7. The device of claim 1, wherein the photoelastic material is configured to rotate a plane of light polarization.

8. The device of claim 1, wherein the stress sensor further comprises a cavity adjacent to the reflector layer or the annular ring.

9. The device of claim 1, wherein the plurality of struts are configured to create measurable deviations in an image reflectance.

10. The device of claim 9, wherein the measurable deviations are usable to quantify changes in an intraocular pressure of the eye.

11. The device of claim 1, wherein the plurality of struts are configured to be used to quantify changes in an intraocular pressure of the eye.

12. The device of claim 1, wherein the reflector material has a thickness of 5 nm or greater.

13. The device of claim 1, wherein the reflector material has a patterned shape.

14. The device of claim 1, wherein the annular ring has varying thicknesses at different locations along a cross section of the annular ring.

15. The device of claim 14, wherein the varying thicknesses are configured to produce different polarization rotations at the different locations.

16. The device of claim 15, wherein a first location having a first thickness comprises a reference region relative to the varying thicknesses at the different locations.

17. The device of claim 16, wherein the reference region is configured to minimize contrast in reflected light when there is no strain, wherein the reference region is configured to allow contrast when there is strain due to a change in intraocular pressure.

18. An intraocular lens for measuring an intraocular pressure (IOP) in an eye, the intraocular lens comprising:
   a body composed of a biocompatible elastomeric material, the body being configured to fit inside the eye;
   a first support leg, the support leg extending radially from the body;
   a photoelastic layer having a central aperture and a plurality of secondary apertures arranged in a ring around the central aperture, the secondary apertures defining a plurality of struts, where in the struts operate as a plurality of stress concentration features, the photoelastic layer being embedded in the body;

a reflector layer having a foot print that substantially matches the photoelastic layer, wherein the reflector layer is adjacent to the photoelastic layer;

a fluid filled cavity adjacent to one of the photoelastic layer and the reflector layer; and wherein the photoelastic layer is configured to deform and produce an optical result in response to changes in the IOP.

19. The intraocular lens of claim 18, wherein the body has a thickness between 2 μm to 1000 μm.

20. The intraocular lens of claim 18, wherein the photoelastic layer is made of a UV curable epoxy.

* * * * *